(12) United States Patent
Burry et al.

(10) Patent No.: US 8,759,385 B2
(45) Date of Patent: Jun. 24, 2014

(54) COMPOSITION COMPRISING AZOLE FUNGICIDE AND WATER SOLUBLE METAL SALT

(75) Inventors: Jason Shaun Burry, Wirral (GB); Richard Livesey Evans, Wirral (GB); Graham Andrew Turner, Wirral (GB)

(73) Assignee: Conopco Inc., Englewood Cliffs, NJ (US)

( * ) Notice: Subject to any disclaimer, the term of this patent is extended or adjusted under 35 U.S.C. 154(b) by 123 days.

(21) Appl. No.: 13/264,759

(22) PCT Filed: Apr. 13, 2010

(86) PCT No.: PCT/EP2010/054815
§ 371 (c)(1),
(2), (4) Date: Oct. 17, 2011

(87) PCT Pub. No.: WO2010/121922
PCT Pub. Date: Oct. 28, 2010

(65) Prior Publication Data
US 2012/0035186 A1    Feb. 9, 2012

(30) Foreign Application Priority Data
Apr. 23, 2009  (EP) .................................. 09158655

(51) Int. Cl.
| | |
|---|---|
| *A01N 43/50* | (2006.01) |
| *A61K 31/415* | (2006.01) |
| *A01N 55/02* | (2006.01) |
| *A61K 31/315* | (2006.01) |
| *C07D 233/54* | (2006.01) |
| *C07D 233/60* | (2006.01) |
| *C07F 3/00* | (2006.01) |

(52) U.S. Cl.
USPC ......... 514/399; 514/494; 548/341.5; 556/131

(58) Field of Classification Search
USPC ............... 514/399, 494; 548/341.5; 556/131
See application file for complete search history.

(56) References Cited

U.S. PATENT DOCUMENTS

| 4,652,445 A * | 3/1987 | Ort ............................. 424/70.14 |
| 6,284,234 B1 | 9/2001 | Niemiec et al. |
| 8,506,942 B2 * | 8/2013 | Burry et al. ..................... 424/74 |
| 2002/0102228 A1 | 8/2002 | Dunlop et al. |
| 2009/0285865 A1 | 11/2009 | Shalaby |

FOREIGN PATENT DOCUMENTS

| DE | 102006037113 A1 | 2/2008 |
| EP | 0489581 A2 | 6/1992 |
| EP | 0674897 A2 | 10/1995 |
| WO | WO 0066072 A1 * | 11/2000 |
| WO | WO0207700 A | 1/2002 |
| WO | WO 2005046629 A1 * | 5/2005 |

OTHER PUBLICATIONS

Tim Faber, Trichogen Complex—Stop Hair Loss and Promote Hair Growth.placeHolder, Ezine Articles, Jun. 3, 2008, Internet Pulication Online, p. 1-p. 2.
PCT International Search Report in PCT Application PCT/EP2010/054815, mailed on Apr. 10, 2010.
EP Search Report in EP Application EP 09 15 8655, dated Sep. 23, 2009.
PCT International Written Opinion in PCT Application PCT/EP2010/054802, (Oct. 25, 2011).
PCT International Written Opinion in PCT Application PCT/EP2010/054815.
Milner et al., Exogen, Shedding Phase of the Hair Growth Cycle: Characterization of a Mouse Model, Journal of Investigative Dermatology, Sep. 2002, 639-644, vol. 119 No. 3.

* cited by examiner

*Primary Examiner* — Sarah Pihonak
(74) *Attorney, Agent, or Firm* — Ronald A. Koatz

(57) ABSTRACT

Hair treatment composition comprising an azole fungicide and zinc gluconate and wherein the composition does not comprise Trichogen®.

1 Claim, No Drawings

COMPOSITION COMPRISING AZOLE FUNGICIDE AND WATER SOLUBLE METAL SALT

The present invention relates to compositions for treating or preventing hair fall.

Despite the prior art there remains a need for improved compositions for treating or preventing hair fall.

Accordingly, there is provided a hair treatment composition comprising an azole fungicide and zinc gluconate, and wherein the composition does not comprise Trichogen® Veg LS 8960.

Preferably, the azole fungicide is climabazole or ketoconazole.

Preferably, the azole is present at from 0.0001 to 1% wt. of the composition.

Preferably, the zinc gluconate is present at from 0.001 to 2% wt. of the composition. More preferably, the composition comprises from 0.005 to 1% wt. of the composition.

Preferably, the composition does not comprises a synergistic mixture of a healthy scalp protein biosynthesis stimulant, a glycosamino production agent, a cell nutrition regulator, a microcirculation promotor and mixtures thereof.

Preferably the composition does not comprises a synergistic trichogenic mixture of a protein biosynthesis stimulant selected from a sulfopeptide of soy, amino acids, glutamine, glutamic acid, hydrolysed protein extracts, particularly sulfopeptides of soy and amino acids, especially tyrosine, arginine, ornithine and citrulline. Preferably, the composition does not comprise a glycosamino production agent selected from the group consisting of glucosamine, L-fucose; fucose rich polysaccharide, xylose, vitamin C, *Eriobotrya japonica* extract, N-acetyl glucosamine, glucosamine sulphate, lysophospholipids, protamine and mixtures thereof. Particularly preferred is glucosamine.

Preferably, the composition does not comprise a cell nutrition regulator especially vitamins of the B group, carnitine, co-enzyme Q10, creatine, taurine, acetyl-carnitine and mixtures thereof. Particularly preferred are vitamins of the B group, especially PP, B5 and biotin.

Preferably, the composition does not comprise a microcirculation promoter, more preferably a microcirculation promoter selected from *Panax Ginseng* Extract, *Arctium Majus* Extract, nitric oxide, niacin, caffeine, *gingko biloba* extract, bicyclic monoterpene diols, α-lipoic acid, ximenynic acid, proanthocyanidins, arginine and mixtures thereof.

Preferably, the composition does not comprise a protein biosynthesis stimulant selected from a sulfopeptide of soy, amino acids, glutamine, glutamic acid, hydrolysed protein extracts.

Preferably, the composition does not comprise a glycosamino production agent selected from glucosamine, L-fucose; fucose rich polysaccharide xylose,vitamin C, *Eriobotrya Japonica* extract, N-acetyl glucosamine, glucosamine sulphate, lysophospholipids, protamine and mixtures thereof.

Preferably, the composition does not comprise a cell nutrition regulator is selected from vitamins of the B group, carnitine, co-enzyme Q10, creatine, taurine, acetyl-carnitine and mixtures thereof.

Preferably, the composition does not comprise a microcirculation promoter is selected from *Panax Ginseng* Extract, *Arctium Majus* Extract, nitric oxide, niacin, caffeine, *gingko biloba* extract, bicyclic monoterpene diols, α-lipoic acid, ximenynic acid, proanthocyanidins, arginine and mixtures thereof.

Most preferably, the composition does not comprise Trichogen® ex Cognis, in particular Trichogen® Veg LS 8960.

Trichogen® Veg LS 8960. contains:

*Panax Ginseng* Root Extract, Arginine, Acetyl Tyrosine, *Arctium Majus* Root Extract, Hydrolysed Soy Protein, Zinc gluconate, Niacinamide, Biotin, *Salvia Sclarea* Extract, *Cinnamomumb Zeylanicum* Extract, *Ginko Biloba* Extract and *Kigela Africanal* Extract.

The composition according to the invention may be in any product form, e.g. shampoo, mousse, conditioner, gel, mask and may be a rinse-off product or a leave-on product.

Depending on product form the composition according to the invention may also comprise any common ingredients typically found in such product form. For example, a shampoo will likely comprise cleansing surfactants; a conditioner will comprise conditioning agents selected from fatty alcohols, silicone and cationic surfactants, etc.

The invention will now be described with reference to the following embodiments.

EXAMPLE 1

The following are formulations according to embodiments of the invention.

Leave-on formulations

|  | A | B | C | D | E | F |
|---|---|---|---|---|---|---|
| Water and minors | To 100% | To 100% | To 100% | To 100% | To 100% | To 100% |
| Natrosol 250HHR | 1.00 | 1.00 | 1.00 | 1.00 | 1.00 | 1.00 |
| Glycerol | 5.00 | 5.00 | 5.00 | 5.00 | 5.00 | 5.00 |
| Zinc gluconate | 0.1 | 0.1 | 0.05 | 0.05 | 0.001 | 0.006 |
| Climbazole | 0.02 | 0.001 | 0.02 | 0.001 | 0.008 | 0.06 |
| Ethanol | 1.0 | 1.0 | 1.0 | 1.0 | 1.0 | 1.0 |

Shampoo examples

| | | | | |
|---|---|---|---|---|
| Water and minors | To 100% | To 100% | To 100% | To 100% |
| Climbazole | 0.5 | 0.5 | 0.5 | 0.5 |
| Zinc gluconate | 1.0 | 0.8 | 0.4 | 0.5 |
| Texapon N70 | 7.70 | 7.70 | 7.70 | 7.70 |
| Mackanate EL | 12.50 | 12.50 | 12.50 | 12.50 |
| Tegobetaine | 9.60 | 9.60 | 9.60 | 9.60 |
| Jaguar C13S | 0.15 | 0.15 | 0.15 | 0.15 |
| Jaguar C17 | 0.05 | 0.05 | 0.05 | 0.05 |
| Sodium Hydroxide (50%) | 0.05 | 0.05 | 0.05 | 0.05 |

Conditioners

| | | |
|---|---|---|
| Water | To 100% | To 100% |
| Lexamine S13 | 1.25 | 1.25 |
| Ganamin BTLF | 1.25 | 1.25 |
| Laurex CS | 5.00 | 5.00 |
| Potassium Chloride | 0.10 | 0.10 |
| EDTA | 0.10 | 0.10 |
| Lauric Acid | 0.30 | 0.30 |
| Zinc gluconate | 1.0 | 1.0 |
| Climbazole | 0.5 | 0.2 |
| Propylene glycol | 2.0 | 2.0 |

EXAMPLE 2

The following shows how zinc gluconate and climbazole provide an improved anti-trypsin effect.

1. Zinc Gluconate (0.00156%) plus climbazole

| Ingredient | Normalised activity | | | | | |
|---|---|---|---|---|---|---|
| Control (Trypsin only) | 1.0 | 1.0 | 1.0 | 1.0 | 1.0 | 1.0 |
| a. Climbazole 0.00391% | | | | | | 1.15 |
| b. Climb 0.00781% | | | | | 1.31 | |
| c. Climb 0.01563% | | | | 1.41 | | |
| d. Climb 0.03125% | | | 1.30 | | | |
| e. Climb 0.0625% | | 0.908 | | | | |
| f. Climb 0.125% | 1.06 | | | | | |
| g. Zinc gluconate (0.00156%) | 1.03 | 1.03 | 1.03 | 1.03 | 1.03 | 1.03 |
| Calculated efficacy | 1.045 | 0.969 | 1.165 | 1.22 | 1.17 | 1.09 |
| Experimental efficacy (synergy) | 0.935 | 0.88 | 0.32 | 0.49 | 0.75 | 0.93 |

2. Zinc Gluconate (0.003125%) plus climbazole

| Ingredient | Normalised activity | | | | | |
|---|---|---|---|---|---|---|
| Control (Trypsin only) | 1.0 | 1.0 | 1.0 | 1.0 | 1.0 | 1.0 |
| a. Climbazole 0.00391% | | | | | | 1.15 |
| b. Climb 0.00781% | | | | | 1.31 | |
| c. Climb 0.01563% | | | | 1.41 | | |
| d. Climb 0.03125% | | | 1.30 | | | |
| e. Climb 0.0625% | | 0.908 | | | | |
| f. Climb 0.125% | 1.06 | | | | | |
| g. Zinc gluconate (0.003125%) | 0.957 | 0.957 | 0.957 | 0.957 | 0.957 | 0.957 |
| Calculated efficacy | 1.01 | 0.9325 | 1.1285 | 1.1835 | 1.1335 | 1.0535 |
| Experimental efficacy (synergy) | 0.87 | 0.88 | 0.24 | 0.27 | 0.61 | 0.83 |

3. Zinc Gluconate (0.00625%) plus climbazole

| Ingredient | Normalised activity | | | | | |
|---|---|---|---|---|---|---|
| Control (Trypsin only) | 1.0 | 1.0 | 1.0 | 1.0 | 1.0 | 1.0 |
| a. Climbazole 0.00391% | | | | | | 1.15 |
| b. Climb 0.00781% | | | | | 1.31 | |
| c. Climb 0.01563% | | | | 1.41 | | |
| d. Climb 0.03125% | | | 1.30 | | | |
| e. Climb 0.0625% | | 0.908 | | | | |
| f. Climb 0.125% | 1.06 | | | | | |
| g. Zinc gluconate (0.00625%) | 0.8404 | 0.8404 | 0.8404 | 0.8404 | 0.8404 | 0.8404 |
| Calculated efficacy | 0.95 | 0.874 | 1.07 | 1.125 | 1.075 | 0.995 |
| Experimental efficacy (synergy) | 0.753 | 1.10 | 0.328 | 0.037 | 0.384 | 0.578 |

The invention claimed is:

1. Hair treatment composition comprising climbazole and zinc gluconate and wherein the composition does not comprise a mixture of *Panax Ginseng* Root Extract, Arginine, Acetyl Tyrosine, *Arctium Majus* Root Extract, Hydrolysed Soy Protein, Zinc gluconate, Niacinamide, Biotin, *Salvia Sclarea* Extract, *Cinnamomumb Zeylanicum* Extract, *Ginko Biloba* Extract and *Kigela Africana* Extract;
   wherein the zinc gluconate and climbazole are present in amounts sufficient to synergistically inhibit trypsin;
   wherein the climbs is present at 0.0001 to 1% by wt. of the composition and the zinc gluconate is present at 0.001 to 0.00625% by wt. of the composition.

\* \* \* \* \*